United States Patent [19]

Shernov et al.

[11] Patent Number: 4,673,569

[45] Date of Patent: Jun. 16, 1987

[54] MOUSSE HAIR COMPOSITION

[75] Inventors: Stephen L. Shernov, Long Valley; Maurice Siegal, Hillsdale; Richard Markowitz, Montvalle, all of N.J.

[73] Assignee: Faberge Incorporated, Mahwah, N.J.

[21] Appl. No.: 700,744

[22] Filed: Feb. 12, 1985

[51] Int. Cl.$^4$ .......................... A61K 7/00; A61K 9/00
[52] U.S. Cl. .............................. 424/47; 424/DIG. 1; 424/DIG. 2
[58] Field of Search ............. 424/47, DIG. 1, DIG. 2

[56] References Cited

U.S. PATENT DOCUMENTS

| | | | |
|---|---|---|---|
| 2,964,165 | 12/1960 | Riley | 424/47 |
| 3,914,403 | 10/1975 | Valan | 424/70 |
| 3,947,557 | 3/1976 | Jones et al. | 424/66 |
| 4,001,392 | 1/1977 | Curry et al. | 424/47 |
| 4,156,657 | 5/1979 | Lin | 106/22 |
| 4,263,275 | 4/1981 | Nandagiri | 424/47 |
| 4,610,874 | 9/1986 | Matravers | 514/881 |

FOREIGN PATENT DOCUMENTS

WO85/01876  5/1985  PCT Int'l Appl. .................... 424/47

OTHER PUBLICATIONS

*Merck Index*, 9th ed., Abst. #3101 (1976).
Sagarin, *Cosmetics Science and Technology*, 2nd ed., vol. 2, pp. 162-163 (1972).
Harry's *Cosmetic Materials*, vol. 2, pp. 357-367 (1963).

*Primary Examiner*—Jerome D. Goldberg
*Assistant Examiner*—Freda L. Krosnick
*Attorney, Agent, or Firm*—Gottlieb, Rackman & Reisman

[57] ABSTRACT

A mousse hair product comprises a body film forming resin and a long chain non-ionic ester for imparting good combability and reducing the static charge of the hair. The non-ionic chemical increases the stability of the composition and in combination with corrosion inhibitors reduces its corrosive effect upon the epoxy coated, tinplated steel aerosol containers.

6 Claims, No Drawings

MOUSSE HAIR COMPOSITION

The present invention relates to a novel composition for a foamed hair product. In particular it relates to mousse hair products that facilitate hairstyling and which have diminished corrosive effects on the aerosol containers for such products. More particularly, it relates to such products in which the principal components are non-ionic materials.

BACKGROUND OF THE INVENTION

So-called mousse hairstyling products have become popular with the public. Such products are dispensed from aerosol cans as a pressure sensitive foam which is released upon the hair, typically after the hair is shampooed and towel dried. A mousse gives an appearance of penetration of the hair as the foam collapses and has ingredients that perform functions that are needed for the improved styling of hair. In particular, some of the purposes of these ingredients are to add body to the hair, thereby making it appear fuller on the head of the user, and to enhance the combability of the hair in order to make it more manageable. In a mousse some of the collapsed foam may be designed to be combed out of the hair during the process of styling.

Mousses are distinguished from hairsprays or hair setting sprays which are typically used during the final step in holding the set of the hair. Such hairsprays tend to form a film, with flexibility provided by plasticizers that allow the hair to have some freedom of motion. Pressurized hair spray is generally a solution of film-producing resins in an alcohol solvent, together with an appropriate propellant, usually packaged in a tin can. When sprayed on the hair, the product forms droplets of resin, which, when dry, impart support and stiffening properties to the individual hair fibers, by forming junctions between adjacent or intersecting hair fibers and thereby yielding a rigid network.

Although hair sprays may be dispensed from an air pump, it is at present not practical to dispense the mousse products other than from an aerosol can. In particular, in forming a foam, it is preferred that at least the foam-forming components of the mousse be dispersed in an aerosol vehicle prior to being dispensed. Mousses are, in general, not alcoholic solvent solutions, but contain substantial quantities of water which introduce problems of corrosion of the aerosol containers.

Despite these differences, the similarity of purpose of the hairsprays and mousses have led prior designers of mousses to include in their products the most efficacious components previously known to them from hair sprays and to neglect the interaction between the product that they were developing and the container from which it would have to be dispensed. As a result, mousses known before the present invention were extremely corrosive and had to be dispersed in relatively expensive aluminum aerosol containers.

This conventional approach has led prior designers to employ quaternary cationic materials in their mousse products to impart combability and control of flyaway of the hair due to static charge. The fact that hair tends to be negatively charged from combing possibly led to the belief that such cationic products would be necessary to adhere the product to the hair, since cationic materials are inherently positively charged.

There has been some suggestion, for hair products to be rinsed from the hair, of employing cationic polymers, but only in conjunction with specific anionic polymers and non-ionic surface-active agents. For example see U.S. Pat. Nos. 4,240,450 and 4,371,517.

The problem with the cationic materials in a mousse is that they attack the material from which the most economical containers could be made, namely, tinplated steel containers.

At present, relatively expensive aluminum cans are employed for mousse type sprays. They cost substantially more than the cost of standard, three-piece steel cans having epoxy coatings.

It is an object of the present invention to provide a mousse hair product that is adapted to be dispensed from epoxy-coated, tinplated steel aerosol containers.

It is a further object of the present invention to provide a composition for a mousse hair product that avoids the corrosive effects of quaternary cationic materials on such aerosol containers.

It is a further object of the present invention to provide a novel mousse product employing a long chain nonionic ester hair styling component.

It is the still further object of the present invention to provide a mousse hair product having the foregoing advantages without detracting from the hair styling properties of the mousse styling product.

SUMMARY OF THE INVENTION

Generally speaking, in accordance with the invention, a mousse hair product comprising a body film forming resin and a long chain non-ionic ester for imparting good combability and reducing the static charge of one's hair is provided. The mousse hair product includes a water-based and an alcohol-based phase. The non-ionic ester is in the alcohol-based phase and increases the stability of the composition. Moreover, the non-ionic ester works in combination with a corrosion inhibitor in the water-based phase to reduce the corrosive effect upon tin plated steel aerosol containers.

The water-based phase includes water as a solvent, a hair styling and body film forming resin, and a corrosion inhibitor. The alcohol-based phase includes a non-ionic ester capable of imparting good combability and eliminating the static charge of the hair, an alcohol as a secondary solvent, and a foam forming chemical. A vapor phase corrosion inhibitor is also added which acts as a buffer for the system. A propellant is used to aerosolize the container.

DETAILED DESCRIPTION OF THE PREFERRED EMBODIMENT

The composition in accordance with the invention comprises non-ionic, long chain esters for components of mousse sprays, which impact combability and control flyaway hair. Because of this, cationic and anionic materials are avoided. The resulting product surprisingly still allows the hair upon which the mousse is applied to have a crisp dry feel and still permits the hair to be easily styled. This is accomplished by including a body film forming resin to give body to the hair together with the long-chained ester.

The principal ingredients of the composition for a mousse will now be described.

The composition in accordance with the invention includes a water-based phase and an alcohol-based phase. The composition, in essence, is a suspension or temporary emulsion of the water-based phase with the alcohol-based phase.

The water-based phase includes water as a solvent, a hair styling and body film forming resin, and a liquid-phase corrosion inhibitor. The alcohol based phase includes a long chain non-ionic ester capable of imparting good combability and eliminating the static charge of the hair, an alcohol as a secondary solvent, and a foam forming chemical. Moreover, a vapor-phase corrosion inhibitor is added to the composition which acts as a buffer for the system.

The hair styling and body film forming resin is polyvinylpyrrolidone. Polyvinylpyrrolidone is soluble in aqueous and alcohol solvent systems.

The liquid-phase corrosion inhibitor is sodium benzoate.

The non-ionic ester which is capable of imparting good combability and eliminating the static charge of the hair is selected from the group which includes diethylene glycol diesters. Specific diethylene glycol diesters that are suitable include:
Diethylene Glycol Dioctanoate/Diisononanoate
Diethylene Glycol Dihexanoate
Diethylene Glycol Dipelargonate/Diisononanoate
Diethylene Glycol Diisodecanoate/Diisononanoate
Diethylene Glycol Diisononanoate
Diethylene Glycol Dilaurate/Diisononanoate
Diethylene Glycol Dineopentanolate/Diisononanoate
Diethylene Glycol Dineopentanoate
Diethylene Glycol Dicaproate/Diisononanoate
Diethylene Glycol Dicaprylate/Diisononanoate An alcohol is part of the alcohol-based phase as a secondary solvent. The alcohol is ethyl alcohol SD40.

The foam forming chemical is polyoxyethylene 10-oleyl ether.

The vapor phase corrosion inhibitor is ammonium hydroxide.

Optionally, an alcohol-based phase body film forming resin may be added to the alcohol-based phase. The alcohol-based phase body film forming resin is butyl ester polycarboxylic/vinyl methyl ether/maleic anhydride (known by the trade name Duraflex).

For the alcohol-based phase, the preferred long-chain ester is diethylene glycol dioctanoate/isononanoate.

Although not critical to the composition, perfume oils may be added to give the product a fragrant property.

Below is recited a specific example of the mousse composition in accordance with the invention.

Example 1:

| Ingredients-water-based phase | % Wt/Wt |
|---|---|
| Deionized Water | 84.300 |
| Polyvinylpyrrolidone K-30 | 3.250 |
| Sodium Benzoate | 0.500 |
| Ethyl Alcohol SD40, 200 deg. | 9.180 |
| Butyl Ester Polycarboxylic/Vinyl Methy Ether/Maleic Anhydride | 0.100 |
| Diethylene Glycol Dioctanoate/Diisononanoate | 1.420 |
| Polyoxyethylene 10-Oleyl Ether | 0.900 |
| Perfume Oil | 0.300 |

These phases are combined with ammonium hydroxide of a pH of about 8.5–9.0 which aids as a buffer to protect the container in which the product is placed from corrosion. Sodium benzoate is also placed on the container as a barrier.

The percentage of weight of ammonium hydroxide is:

| Ammonium Hydroxide | 0.050 |
|---|---|

An aerosol is required for sufficient foaming. The components of the mousse are solubilized or emulsified with the aerosol material.

The fill requirements are percentages by weight:

| Concentrate | 90.00 |
|---|---|
| Propellant | 10.00 |

A three-piece steel aerosol container is filled with this product according to the above stated fill requirements.

A. The following are the ranges within which the composition in accordance with the invention remains effective:

| Water-based Phase | |
|---|---|
| Deionized water | Make up to 100% |
| Polyvinylpyrrolidone K-30 | 0.5–10.0 |
| Sodium benzoate | 0.2–2.0 |
| Alcohol-based Phase | |
| Ethyl alcohol SD40.200 deg. | 0.5–20.0 |
| Butyl ester Polycarboxylic/vinyl Methyl ether/maleic anhydride (not necessary) | 0.0–8.0 |
| Diethylene glycol Dioctonoate/diisononanoate | 0.20–6.0 |
| Polyoxyethylene 10-oleyl ether | 0.2–5.0 |
| Perfume oil | Not critical |

These phases are combined with:

| Ammonium hydroxide | 0.01–1.0 |
|---|---|

The fill requirements are:

| Concentrate | Make up to 100% |
|---|---|
| Propellant | 5–30 |

B. The following are the ranges that are preferred:

| Water-based Phase | |
|---|---|
| Deionized water | Make up to 100% |
| Polyvinylpyrrolidone K-30 | 1–6 |
| Sodium benzoate | 0.4–1.0 |
| Alcohol-based Phase | |
| Ethyl alcohol SD40, 200 deg. | 2–15 |
| Butyl ester polycarboxylic/vinyl methyl ether/ maleic anhydride (not necessary) | 0.05–4.0 |
| Diethylene glycol dioctanoate/ diisononanoate | 0.05–4.0 |
| Polyoxethylene 10-oleyl ether | 0.6–2.5 |
| Perfume oil | 0.0–2.0 |

These phases are combined with:

| Ammonium hydroxide | 0.02–0.2 |
|---|---|

The fill requirements are:

| Concentrate | 90.00 |
|---|---|
| Propellant | 10.00 |

The preferred range of propellant by percentage weight is 8–20%.

The method of manufacture of the product comprises adding water, sodium benzoate and polyvinylpyrrolidone into a stainless steel mixing tank and mixing until dissolved. Then the ethyl alcohol, polyoxyethylene 10-oleyl ether, butyl ester polycarboxylic/vinyl methyl ether/maleic anhydride and diethylene glycol dioctanoate/diisononanoate are added into a stainless steel mixing tank and mixed until dissolved.

Thereafter, ammonium hydroxide is added and the mixture is mixed until uniform. Finally, an aerosol or propellant is added. Isobutane is the preferred propellant to aerosolize the product. Other propellants that are familiar to persons of ordinary skill in this art may also be used.

An aerosol container that is preferred for use with this invention is a three-piece welded tinplate aerosol container having an internal lining of double epoxy and an epoxide or lacquered side seam stripe (internal). The aerosol nozzle can be selected to provide whatever distribution is desired in a manner known to persons of ordinary skill in this art.

One preferred valve is a 1" tinplate aerosol can valve having a stem size of $2 \times 0.020"$; a Buna N stem gasket having an inverted body and; a mounting cup made of tinplate having a conical shape. The valve may be epoxy coated. The preferred actuator is a vertical foam spout.

In testing upon the hair of volunteers, the composition in accordance with the invention has improved styling properties relative to existing commercial products. Particularly advantageous is the lack of corrosive effect of the non-ionic, long chain ester in combination with corrosion inhibiting components. This is especially significant in view of the long felt need to reduce the corrosive effects of products supplied in aerosol cans. Aerosol shampoos, which had been one of the first of the aerosol hair products to be produced, had to be withdrawn from the market and never reappeared as a commercially successful product. Their original failure was due to the corrosive effect of the ingredients upon the netal containers.

Aerosol shampoos had a very short shelf life because of can corrosion within months of production, U.S. patent 2,878,231 disclosed a pressurized liquid shampoo for employment in an aerosol.

A typical mousse product that existed before the present invention contained a cationic quat material, for example Celquat 200 that is corrosive to steel cans, even with the addition of corrosion inhibitors or the various epoxy coatings on the can. This is not to imply that it is impossible to adequately coat the interior of a steel container to resist quat formulations, but rather than the present invention permits conventional double epoxy coated steel cans to be used where the quat formulations did not allow such use.

The aluminum cans that had been used with those products still had to be coated with an organisol coating.

Although the present invention has been described in terms of various preferred embodiments, the invention is limited only by the following claims:

We claim:

1. A composition for use on human hair adapted to be dispensed as a pressure sensitive foam by use of a propellant, comprising:
   a. a water-based phase comprising water, polyvinylpyrrolidone K-30 in an amount between about 1 and 6 weight percent, and sodium benzoate in an amount between about 0.4 and 1.0 weight percent;
   b. an alcohol-based phase comprising diethylene glycol dioctanoate/diisononanoate in an amount between about 0.05 and 4.0 weight percent, ethyl alcohol SD40 in an amount between about 2 and 15 weight percent, polyoxethylene 10-oleyl ether in an amount between about 0.6 and 2.5 weight percent and butyl ester polycarboxylic/vinyl methyl ether/maleic anhydride in an amount about between 0.05 and 4.0 weight percent; and
   c. ammoniun hydroxide in an amount between about 0.02 and 0.2 weight percent; the weight percents based on the total weight of the composition.

2. The composition of claim 1, further including a perfume oil in the alcohol-based phase in an amount between about 0.0 and 2.0 weight percent.

3. A composition for use on human hair adapted to be dispensed as a pressure sensitive foam by use of a propellant, comprising:
   a. a water-based phase comprising water, polyvinylpyrrolidone K-30 in an amount between about 0.5 and 10.0 weight percent, and sodium benzoate in an amount between about 0.2 and 2.0 weight percent;
   b. an alcohol-based phase comprising a diethylene glycol diester in an amount between about 0.2 and 6.0 weight percent, ethyl alcohol SD40 in an amount between about 0.5 and 20.0 weight percent and polyoxethylene 10-oleyl ether in an amount between about 0.2 and 5.0 weight percent; and
   c. ammonium hydroxide in an amount between about 0.01 and 1.0 weight percent, the weight percents based on the total weight of the composition.

4. The composition of claim 3, wherein the alcohol-based phase further comprises butyl ester polycarboxylic/vinyl methyl ether/maleic anhydride in an amount between about 0.0 and 8.0 weight percent.

5. The composition of claim 3, wherein the diester is selected from the group including diethylene glycol dioctanoate/diisononanoate, diethylene glycol dihexanoate, diethylene glycol dipelargonate/diisononanoate, diethylene glycol diisodecanoate/diisononanoate, diethlene glycol diisononanoate, diethlene glycol dilaurate/diisononanoate, diethylene glycol dineopentanoate/diisononanoate, diethylene glycol dineopenanoate, diethylene glycol dicaproate/diisononanoate, and diethylene glycol dicaprylate/diisononanoate;

6. The composition of claim 5, wherein the diester is diethylene glycol dioctanoate/diisononanoate.

* * * * *